US005654502A

United States Patent [19]
Dutton

[11] Patent Number: 5,654,502
[45] Date of Patent: Aug. 5, 1997

[54] AUTOMATIC WELL TEST SYSTEM AND METHOD OF OPERATING THE SAME

[75] Inventor: Robert E. Dutton, Louisville, Colo.

[73] Assignee: Micro Motion, Inc., Boulder, Colo.

[21] Appl. No.: 579,807

[22] Filed: Dec. 28, 1995

[51] Int. Cl.[6] .......................... G01F 13/00; G01N 33/00
[52] U.S. Cl. ...................... 73/152.18; 73/861.04; 73/19.1; 73/861.357
[58] Field of Search .................. 73/155, 152, 861.04, 73/861.357, 19.1, 152.18

[56] References Cited

U.S. PATENT DOCUMENTS

| | | | |
|---|---|---|---|
| 3,934,275 | 1/1976 | Bishton, Jr. | 4/10 |
| 4,429,581 | 2/1984 | Furmaga | 73/861.04 |
| 4,689,989 | 9/1987 | Aslesen et al. | 73/61.1 B |
| 4,773,257 | 9/1988 | Aslesen et al. | 73/61.1 |
| 4,776,210 | 10/1988 | Baille et al. | 73/61.1 R |
| 4,852,395 | 8/1989 | Kolpak | 73/61.1 R |
| 4,881,412 | 11/1989 | Northedge | 73/861.04 |
| 5,029,482 | 7/1991 | Liu et al. | 73/861.04 |
| 5,090,238 | 2/1992 | Jones | 73/155 |
| 5,090,253 | 2/1992 | Kolpak | 73/861.38 |
| 5,127,272 | 7/1992 | Dean et al. | 73/861.04 |
| 5,253,533 | 10/1993 | Lam et al. | 73/861.37 |
| 5,535,632 | 7/1996 | Kolpak | 73/861.04 |

*Primary Examiner*—Hezron E. Williams
*Assistant Examiner*—J. David Wiggins
*Attorney, Agent, or Firm*—Duft, Graziano & Forest, P.C.

[57] ABSTRACT

An automatic well test system (20) utilizes a Coriolis flowmeter (68) that functions as a mass flowmeter and densitometer in combination with a water-cut monitor (66) to calculate volumetric flow rates and densities of materials draining from a test separator (24) in a combined or two-phase production stream. An oil-phase density value is corrected to eliminate the effect of its water content, and divided into the mass flow rate reading to obtain a net oil flow rate. System operations are governed by an automated controller (86) that utilizes a gas blanket system (28) to prevent low pressures from liberating gas from the liquids within the test separator.

15 Claims, 2 Drawing Sheets

FIG. 1

AUTOMATIC WELL TEST SYSTEM AND METHOD OF OPERATING THE SAME

BACKGROUND OF THE INVENTION

1. Field of the Invention

The present invention pertains to the field of automated oilfield separator systems for use in measuring production volumes including a mixture of oil, gas, and water components. More specifically, the separator system utilizes a Coriolis flowmeter, a densitometer, and a water-cut probe to measure production volumes of the respective components or phases of the production mixture.

2. Statement of the Problem

Oil and gas wells reach beneath the earth's surface to drain rock formations where producible quantities of oil and gas have become trapped. Oil, gas, and water can simultaneously flow into the well from a single producing formation. This multiphase flow of oil, gas, and water results in a production mixture that may be separated into its respective components. It is desirable to separate the production mixture including oil, gas, and water components into its respective components because commercial markets normally exist for only the oil and gas. No market exists for the Water because it is typically saltwater that can create a disposal problem. Oil and gas production is often associated with the production of a significant amount of water because it is commercially feasible to produce these wells until the pumping costs plus the cost of saltwater disposal exceed the revenue derived from oil and gas sales.

An oilfield typically extends over a plurality of mineral-right leases. Each lease or a group of leases typically has an operator that oversees the efforts to produce a particular set of wells. The operator must acquire well test data before the operator can properly manage the lease. Well test data includes wellhead pressure data, as well as the volumetric flow rates for the respective oil, gas, and water components of a production mixture that originates from a single well. The lease operator requires well test information for a proper allocation of the revenue derived from each producing well among the various ownership interests in that well. Additionally, the lease operator requires well test information to conduct engineering studies that attempt to optimize the production performance of the field as a whole. For example, an engineer could choose to shut-in oil production from a well having an excessively high water cut, and convert the well into a water injection well to assist an ongoing waterflood.

The producing wells in an oilfield or a portion of an oilfield often share a production facility including a main production separator, a well test separator, pipeline transportation access, saltwater disposal wells, and safety control features. The use of common or shared production facilities prevents the operator from having to spend additional capital for redundant facilities.

The test separator is used to facilitate the measurement of volumetric flow rate information from the production materials that derive from a single well. The measurements include volumetric flow rates of the respective oil, gas, and water phases, e.g., 95 barrels of water per day, 5 barrels of oil per day, and 6 MCF of gas per day. Another useful measurement is the 'water-cut' measurement. The term 'water-cut' is hereby defined as any ratio that represents a relationship between a volume of oil and a volume of water in an oil and water mixture. According to the most conventional usage of the term 'water-cut', well production fluids in the above example would have a 95% water-cut because water comprises 95 of the total 100 barrels of oil and water liquids. The term 'water-cut' is sometimes also used to indicate a ratio of the total volume of oil produced to the total volume of water produced. A term 'oil-cut' could imply the oil volume divided by the combined oil and water volume. As defined herein, the term 'water-cut' encompasses all of these alternative definitions.

The main production separator and the well test separator are each used to separate the respective oil, gas, and water components that arrive at the production facility as a mixture of these phases or components. The main production separator receives combined production volumes from multiple wells to prepare these volumes for eventual sale. The test separator typically has a reduced throughput capacity in comparison to the main production separator, and is provided for use in measuring production rates that derive from a single well. As used herein, the term "phase" refers to a type of fluid that may exist in contact with other fluids, e.g., a mixture of oil and water includes a discrete oil phase and a discrete water phase. Similarly, a mixture of oil, gas, and water includes a discrete gas phase and a discrete liquid phase with the liquid phase including an oil phase and a water phase. Industry terminology refers to a 'two-phase' separator as one that is used to separate a gas phase from a liquid phase including oil and water. A 'three-phase' separator is used to separate the gas from the liquid phases and also separates the liquid phase into oil and water phases.

As compared to two phase separators, three phase separators require additional valve and weir assemblies, and typically have larger volumes to permit longer residence times of produced materials for gravity separation of the production materials into their respective oil, gas, and water components. The use of a three phase test separator permits direct measurement of the separated components. Error exists even in this direct measurement because water is seldom, if ever, completely removed from the segregated oil component at the production facility. A residual water content of up to about ten percent typically remains in the segregated oil component even after a separator is used to remove most of the water from the oil component.

Two phase separators cost less, halve a much simpler design, and require less maintenance than do three phase separators. The use of a two phase separator typically does not permit direct volumetric measurements to be obtained from the segregated liquid (oil and water) components under actual producing conditions. The use of a single Coriolis flowmeter in combination with a two phase separator advantageously permits measurement of the respective oil and water volumes in the liquid phase leaving the test separator.

The use of a capacitance or resistance probe to measure water-cut in produced fluids is known in the industry. These water-cut monitors operate on the principle that oil and water have drastically different dielectric constants. Thus, a water-cut probe can measure the volumetric percentage of water in a combined oil and water flow stream. These monitors, however, provide acceptably accurate water-cut measurements only where the water volume is less than about 20% to 30% of the total flow stream. The upper 30% accuracy limit is far below the level that is observed from many producing wells. For example, the total liquid production volume of an oil well can be 99% water. Water-cut monitors, therefore, are relegated to determining the water-cut in an oil component that has a low water content. Water-cut monitors most often cannot be used to determine the water content in the material that flows from a two phase separator because the total liquid component has a water content that exceeds the 30% upper accuracy limit.

It is necessary to convert the Coriolis-based mass flow rates into volumes because oilfield production is conventionally sold as volume, not mass. Conventional Coriolis meters have a variety of capabilities in addition to their ability to perform mass flow rate measurements. The structure of a conventional Coriolis mass flowmeter can also be operated as a vibrating-tube densitometer because the mass flowmeter works on the principle of vibrating tubes that act as a spring and mass system. These density values are used to convert the total mass flow rate measurements into volumetric values. Nevertheless, the volumetric measurement pertains to the total combined flow stream.

Numerous difficulties exist in using a Coriolis flowmeter to identify the respective mass percentages of oil, gas, and water in a total combined flow stream. A Coriolis mass flowmeter can be used to determine the total mass flow rate and allocate the total mass flow rate to the respective components or phases in the combined flow stream. This calculation technique is especially useful in determining the mass distribution of two phase (e.g., oil and water) flows. Even so, the technique, presently requires laboratory analysis of manually obtained samples to provide density data for use in the volumetric flow rate and water-cut calculation.

U.S. Pat. No. 5,029,482 teaches the use of empirically-derived correlations that are obtained by flowing combined gas and liquid flow streams having known mass percentages of the respective gas and liquid components through a Coriolis meter. The empirically-derived correlations are then used to calculate the percentage of gas and the percentage of liquid in a combined gas and liquid flow stream of unknown gas and liquid percentages based upon a direct Coriolis measurement of the total mass flow rate.

U.S. Pat. No. 4,773,257 teaches that a water fraction of a total oil and water flow stream may be calculated as set forth below in Equation (1):

$$X_w = (D_e - D_{o,T})/(D_{w,T} - D_{o,T}),\tag{1}$$

wherein $X_w$ is a mass-based fraction of water in the total combined oil and water flow stream; $D_e$ is a density of the total combined oil and water flow stream at a measurement temperature T; $D_{oT}$ is a known density of the pure oil component in the total combined flow stream at measurement temperature T; and $D_{w,T}$ is a known density of water in the total combined flow stream at measurement temperature T. The values $D_{o,T}$ and $D_{w,T}$ can be corrected for temperature effects according to Equations (2) and (3) below:

$$D_{o,T} = D_o^* - C_o(T - Tr)\tag{2}$$

$$D_{w,T} = D_w^* - C_w(T - Tr),\tag{3}$$

wherein $D_o^*$ is an oil density at a reference temperature $T_r$ (which is conventionally chosen as 60° F.); $D_w^*$ is a water density at the reference temperature $T_r$; $C_o$ is a thermal expansion coefficient for oil; $C_w$ is a thermal expansion coefficient for water; and the remaining variables are defined above. Those skilled in the art will understand that the thermal expansion coefficients $C_o$ and $C_w$, as well as other correlations that correct densities for temperature, can be obtained from various sources including publications by the American Petroleum Institute.

A total volumetric flow rate is calculated according to Formula (4):

$$Q_e = M_e/D_e,\tag{4}$$

wherein $Q_e$ is a Coriolis-based mass flow rate measurement obtained from the total combined oil and water flow stream; and the remaining terms are defined above.

A volumetric flow rate of oil is calculated according to Equation (5):

$$Q_o = Q_e(1 - X_w),\tag{5}$$

wherein $Q_o$ is a volumetric flow rate of oil, and the remaining variables are defined above.

A volumetric flow rate of water is calculated according to Equation (6):

$$Q_w = Q_e * X_w,\tag{6}$$

wherein $Q_w$ is a volumetric flow rate of water, and the remaining variables are defined above.

The volumetric flow rate values $Q_o$ and $Q_w$ can be corrected to a standard reference temperature, $T_r$, through multiplication of the volumetric flow rate values by the density at a measurement temperature and dividing by the density at the reference temperature, e.g., as in Formula (7):

$$Q_o^* = Q_{o,T} * D_{o,T}/D_o^*,\tag{7}$$

wherein $Q_o$ is a volumetric oil flow rate at a standard reference temperature $T_r$; $Q_{o,T}$ is a volumetric oil flow rate measured at temperature T and calculated according to Equation (5); and the remaining variables are defined above.

A significant problem exists in the use of Equations (1)–(7) because the density values $D_{o,T}$ and $D_{w,T}$ must be measured from samples that are manually obtained from a specific producing well. In the absence of laboratory measurements, it remains impossible to convert the phase-adjusted mass flow rate information into oil and water volumes because the Coriolis meter cannot produce an oil density and a water density value by direct measurement of the combined flow stream. The circumstances under which the samples are taken oftentimes provide a source of error in the laboratory measurements because the sample is exposed to atmospheric pressure. The exposure to atmospheric pressure removes gas from solution, and the resultant sample has a relatively increased density as compared to the former pressurized sample. Additionally, it is nearly impossible to provide laboratory measurement conditions that replicate the field conditions. The density values of produced fluids often change over the life of a producing well. Therefore, periodic sampling of the production fluids is required. The laboratory measurements are, accordingly, disposed to inherent error for lack of timeliness in sampling the fluids and an inability to replicate production line conditions in the laboratory.

A direct density measurement derived from the Coriolis meter cannot be used in the volumetric calculation because it is most often impossible to obtain a satisfactory direct density measurement from the separate oil component. Even if a separator is used to separate the oil component from the water component, the separated oil phase retains up to about ten percent water by volume. The residual water causes an error in the direct density measurement.

Another source of volumetric inaccuracy in Well test measurements pertains to solution gas that is liberated at reduced pressures. The pressure-volume-temperature behavior of the produced fluid can cause appreciable differences in the measured quantities of separated oil and gas that are obtained from the production mixture. A reduced pressure will liberate gas from the oil phase. An increased pressure drives gas back into solution. It is, accordingly, desirable that the test separator conditions approximate the conditions of the main production separator.

The pressure within the test separator may be different from that in the main production separator. Two phase well test separators often flash the production fluid by liberating gas from the fluid at reduced pressure as the liquids are drained from the separators. No effort is made to control the test separator pressure while the liquids are drained because it is commonly believed that the separated production components will be recombined in the main production separator for eventual sale. The failure to control test pressures results in erroneous volumetric measurements because the reduced gas pressure causes solution-gas to leave the oil phase. The liquid volume is, accordingly, reduced, and the liquid has a greater density.

A true need exists for a Coriolis-based flowmeter that can measure volumetric flow rates for the respective phases or components in a total production stream without requiring laboratory measurements on hand samples of the production stream to provide the density values for the respective components. Additionally, there is a need for a test separator system that utilizes sales line or main production separator conditions throughout its measurement cycle to preserve the integrity of the volumetric test measurements.

SOLUTION

The present invention overcomes the problems that are outlined above by providing a fully automated Coriolis-based well test system which does not require manual sampling or laboratory analysis of the production fluids in order to determine the density of the oil and gas components. Additionally, the test system eliminates volumetric measurement errors that derive from the liberation of solution gas at reduced pressures.

The well test system of the invention has two modes of operation. The test system operates as a normal well test system to measure the volume of respective components that are separated from a component mixture, namely, a wellhead production material including oil, gas, and water components. The well test system also has a special density determination mode that avoids the need to obtain hand samples of the production fluids for density measurements. The on-site density measurements obtained from the system are more accurate than laboratory measurements because the fluids are measured at line conditions.

The system includes a test separator that receives wellhead production and separates the mixture into its separate components. A valve manifold is used to selectively fill the test separator with the production of a single well. The test separator is used to retain a mixture of oil, gas, and water phases or components while the forces of gravity segregate these components from the production mixture. A dump valve is opened to at least partially drain the liquid components of the production component mixture from the test separator after separation of the respective components. A Coriolis flowmeter (including a mass flowmeter and a densitometer) is used to measure the mass flow rates of the respective oil and water components as they leave the test separator. The densitometer is used to obtain a density reading of a segregated oil component within the test separator. A water-cut monitor is used to obtain water-cut readings of the segregated oil phase. Altogether, fluid density, temperature, mass flow rate, and water-cut measurements are used to calculate a volumetric flow rate for the oil and water components in the production stream. This correction results in a more accurate calculated for the volumetric oil flow rate.

In preferred embodiments, volumetric test errors are also minimized by connecting a pressurized gas source to the test separator. The gas blanket provided by this pressurized gas source is used to maintain a substantially constant separator pressure even when the separator dump valve is permitting flow of liquids from within the test separator.

Other salient features, objects, and advantages will be apparent to those skilled in the art upon a reading of the discussion below in combination with the accompanying drawings.

DETAILED DESCRIPTION OF THE PREFERRED EMBODIMENT

Figure 1:
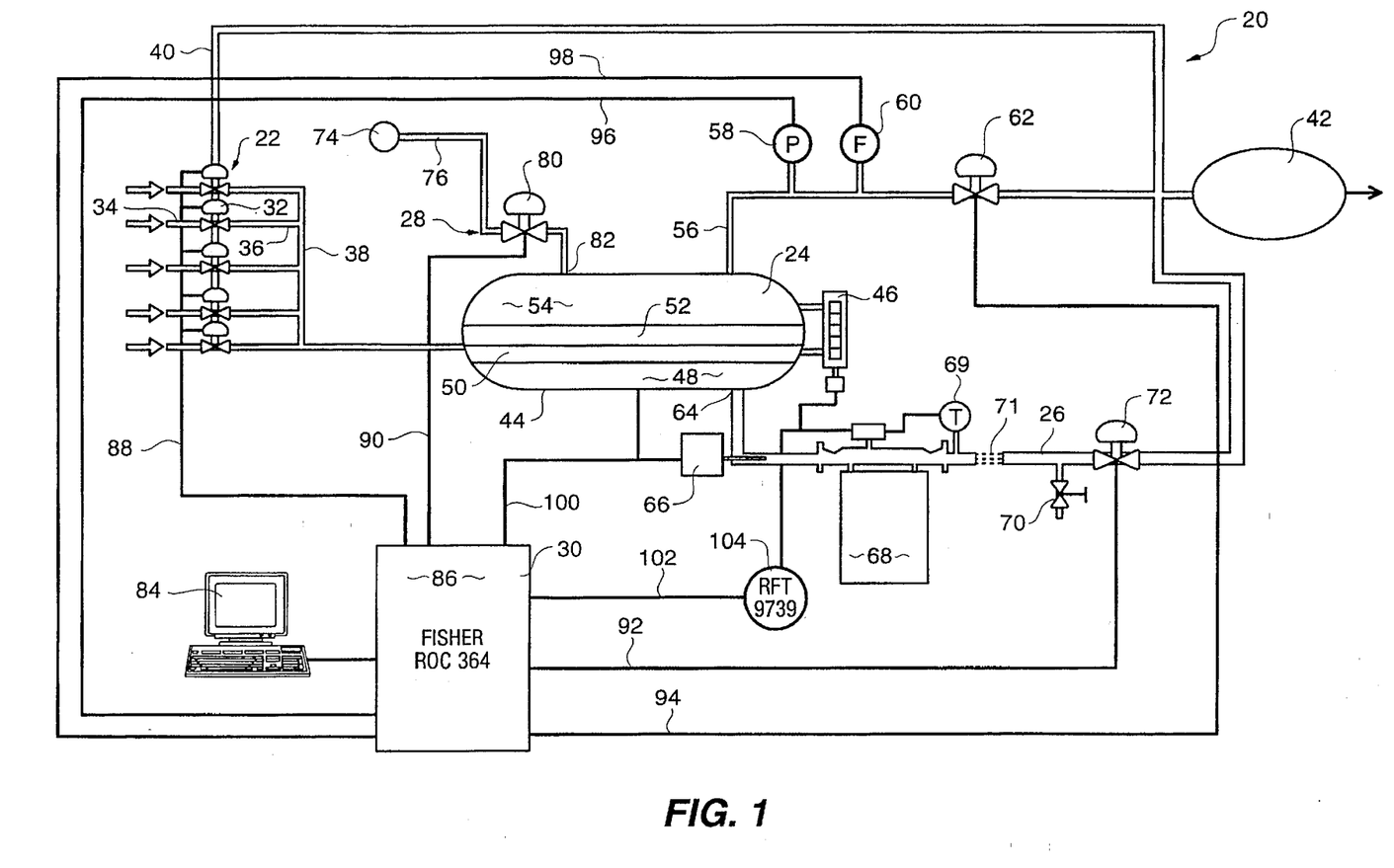
FIG. 1 depicts a schematic layout of an automated well test system according to the present invention.

FIG. 1 depicts automated well test system 20. The major components of system 20 include valve manifold 22 for use in selectively flowing individual wells, test separator 24, flow rate instrumentation drain line 26 for use in measuring volumetric flow rates of production components coming from test separator 24, gas blanket system 28 for use in maintaining a constant pressure in test separator 24, and automation system 30. The individual components of test system 20 may be purchased from a variety of commercial sources and assembled as the configuration shown in FIG. 1.

Valve manifold 22 includes a plurality of valves, e.g., valve 32. Each valve is coupled with a wellhead supply line, e.g., supply line 34, which leads to a single producing well (not depicted). Each valve is coupled with a test separator supply line, e.g., line 36, leading to test separator gathering line 38. Each valve is also coupled with a main production separator gathering line 40 leading to a conventional main production separator 42. The valves, such as valve 32, are preferably-three-way electronically-initiated, pneumatically actuated valves that control access to test separator line 38 and main production separator gathering line 40. Valves 32 are used to direct the production of an individual well to either main production separator 42 or test separator 24. A particularly preferred three way valve for use in this application is the Xomox TUFFLINE 037AX WCB/316 well switching valve with a MATRYX MX200 actuator. The valves are preferably configured to each receive production fluids from a corresponding individual well. The valves can selectively divert the production fluids to main production separator gathering line 40 where the fluids are combined with fluids from other valves for transport to main production separator 42. A single valve can be selected to divert the production from its associated well to test separator gathering line 38 for transport to test separator 24.

Test separator 24 is a conventional well test gravitational separator having an ovaloid outer wall 44 of sufficient strength to withstand well test pressures. Test separator 24 is provided with an electronic liquid level indicator 46 for use in indicating to automation system 30 the level of total liquid including water 48, oil-in-water emulsion 50, and oil 52. Gas 54 resides within test separator 24 above the total liquid level. An exemplary form of level indicator 46 is the Fisher Model 249B-2390 analog float system level transmitter with a sight glass. Test separator 24 is connected to a flue gas drain line 56, which preferably includes a gage pressure transmitter 58, e.g., a Model 2088 pressure transmitter from Rosemount of Eden Prairie, Minn. Flue gas drain line 56 also preferably includes a gas flowmeter 60, such as a smart vortex meter Model 8800 from Rosemount of Eden Prairie, Minn., or an orifice differential pressure transmitter such as the Model 3051 from Rosemount of Eden Prairie, Minn. Electronically controlled gas flow control throttle valve 62 governs the flow of gas through gas drain line 56. Valve 62 may, for example, be purchased as a Model V2001066-ASCO valve from Fisher of Marshalltown, Iowa. Gas drain line 56 terminates in the main production separator 42.

Flow rate instrumentation drain line 26 connects with a drain point 64 on test separator 24. Instrumentation drain line 26 includes a water-cut monitor 66, which uses electrical measurements to quantify the water-cut of fluids flowing through instrumentation drain line 26. Water and oil have very different dielectric constants, which make possible the use of electrical measurements to quantify the water-cut. Thus, water-cut monitor 66 can utilize capacitance, resistance, or other measurements to quantify the water-cut. Other commercially available devices include the use of microwave radiation to detect water cut. An exemplary form of water cut monitor 66 is the Drexelbrook Model CM-2 capacitance monitor. Instrumentation drain line 26 proceeds from water cut monitor 66 to liquid flowmeter 68. Liquid flowmeter 68 preferably includes a Coriolis flowmeter (including a mass flowmeter, densitometer, and temperature gauge), which obtains mass flow, density, and flowmeter temperature measurements of materials passing through instrumentation drain line 26. Exemplary forms of flowmeter 68 include the ELITE Models CMF300356NU and Model CMF300H551NU, which are available from Micro Motion of Boulder, Colo. Temperature sensor 69 is provided to measure the temperature of fluids within instrumentation drain line 26. An exemplary form of temperature sensor 69 is the Model 68 sensor from Rosemount of Eden Prairie, Minn. Sample port 70 is a manually operated valve that is provided for obtaining samples of the fluids within line 26. In-line static mixer 71 is used to ensure that well-mixed samples are obtained from line 26 through port 70.

Dump valve 72 is prefer:ably electronically controlled and pneumatically actuated. Dump valve 72 can be opened to drain test separator 24 through instrumentation drain line 26, and can be closed to permit test separator 24 to fill with production from valve manifold 22. An exemplary form of dump valve 72 is the Fisher level control valve Model EZ-667-ASCO valve. Instrumentation drain line 26 terminates in main production separator 42.

Gas blanket system 28 includes a pressurized gas source 74, which can be gas from a compressor or fuel gas from a pressurized gas source that is used to operate the production facility. The gas source 74 could also be the main production separator 42. Source 74 flows into gas supply line 76, which leads to gas blanket valve 80. An exemplary form of valve 80 is the Fisher Model 357–546. Valve 80 preferably works to maintain a constant pressure within test separator 24, as needed, by throttling a flow of gas through supply line 76. Supply line 76 terminates at upper entry point 82 into test separator 24.

Automation system 30 is used to govern the operation of system 20. System 30 includes a computer 84 (e.g., an IBM 486 compatible machine) that is programmed with data acquisition and programming software. A preferred form of this software is the Intellution software DMACS, which is available from INTELLUTION, a subsidiary of Emerson Electric. This software is particularly preferred because it can generate alarms that indicate abnormal well test conditions representative of mechanical failures which are potentially dangerous. Computer 84 controls programming of remote operations controller 86, which includes a plurality of drivers and interfaces that permit computer 84 to interact with remote components of system 20. A preferred form of remote operations controller 86 is the Fisher Model ROC364. Controller 86 may also be programmed with software to facilitate the implementation of control instructions from computer 84. Valve control leads 88, 90, 92, and 94 respectively connect controller 86 with corresponding electronically actuated valves 32, 80, 72, and 62 for selective control of the valves. Lead 96 connects controller 86 with pressure transmitter 58. Lead 98 connects controller 86 with gas flowmeter 60. Lead 100 connects controller 86 with water-cut meter 66. Lead 102 connects controller 86 with transmitter 104 which, in turn, connects with fluid level 46, liquid flowmeter 68, and temperature sensor 69 for transmitting information to controller 86. An exemplary form of transmitter 104 is the ELITE Model RFT9739, which is available from Micro Motion of Boulder, Colo.

Figure 2:
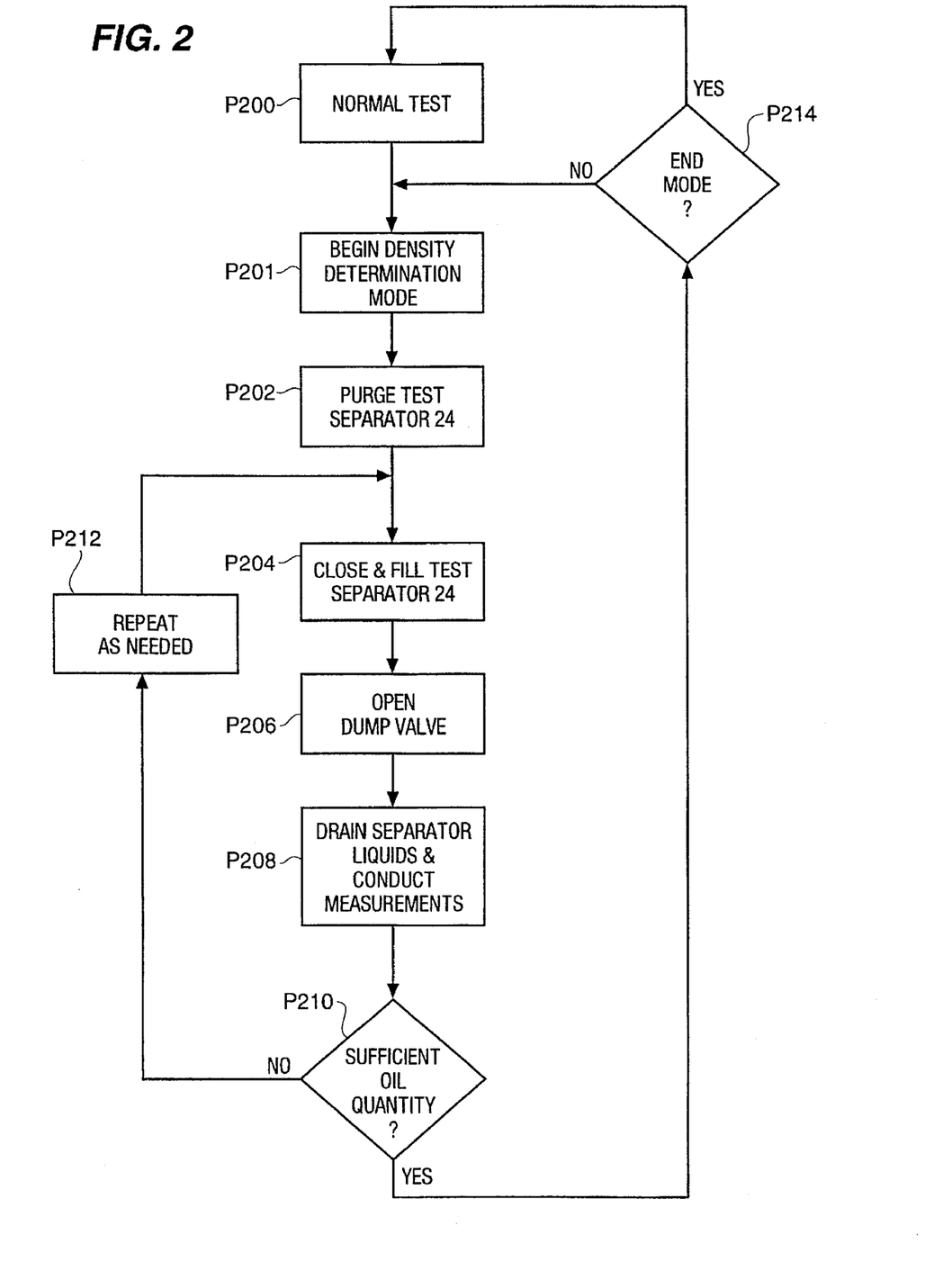
FIG. 2 depicts a flow chart diagram governing the operation of the FIG. 1 system.

FIG. 2 depicts a schematic process control diagram governing the operation of test system 20. The FIG. 2 process is governed by control software in computer 84 or controller 86. Step P200 represents a normal test mode that may optionally include testing a selected well by adjusting manifold 22 to flow the well through test separator 24, or using valve manifold 22 to bypass test separator 24 by flowing all production to main production separator 42 in the event that no test is needed.

In step P200, the lease operator needs to know with accuracy and precision the volumetric oil flowrate $Q_o$ as defined above by Equation (5) and the volumetric water flow rate as defined $Q_w$ by Equation (6). Calculation of these values requires the calculation of a water fraction, such as $X_w$ as defined by Equation (1). In Equation (1), flowmeter 68 can only provide the combined density reading $D_e$ while a given well is on test. Therefore, Equation (1) relies upon laboratory measurements to provide $D_{o,T}$ and $D_{w,T}$. As indicated above in the Background of the Invention, these laboratory measurements sometimes lack accuracy and precision because the laboratory conditions do not correspond to the conditions (e.g., pressure, temperature, and solution gas content) within test system 20.

According to the present invention, the values $D_{o,T}$ and $D_{w,T}$ or Equation (1) are replaced with the values $\rho_{o,T}$ and $\rho_{w,T}$ according to Equation (8):

$$X_w = (D_e - \rho_{o,T})/(\rho_{w,T} - \rho_{o,T}), \qquad (8)$$

wherein $\rho_{o,T}$ is a density of the pure oil phase excluding any residual water content of the segregated oil component; $\rho_{w,T}$ is a density of the pure water phase; and the remaining variables are defined above. The variables $\rho_{o,T}$ and $\rho_{w,T}$ of Equation (8) differ from the variables $D_{o,T}$ and $D_{w,T}$ of Equation (1) because the variables $D_{o,T}$ and $D_{w,T}$ derive from laboratory measurements that are conducted upon samples that are obtained manually, e.g., in a flow laboratory after removal from system 20 through spigot 70. In contrast, the variables $\rho_{o,T}$ and $\rho_{w,T}$ derive from in-line measurements that flowmeter 68 conducts on materials within test system 20.

The discussion below pertaining to Steps 201–214 describes how to obtain the in-line measurements of $\rho_{o,T}$ and $\rho_{w,T}$. These values have significance because each of Equations (1)–(7) yields a superior (more accurate) calculation by substituting $\rho_{o,T}$ for $D_{o,T}$, and by substituting $\rho_{w,T}$ for $D_{w,T}$, as has been done for Equation (1) in the case of Equation (8). This substitution provides greater accuracy in the calculations because the in-line density measurements eliminate the need for error-prone laboratory measurements in the calculation of $D_{o,T}$ and $D_{w,T}$. In contrast, Equation (1) relies upon error-prone laboratory measurements that sometimes fail to reflect in-line conditions.

Flowmeter 68 is preferably programmed to perform calculations according to Equations (2)–(8) by substituting $\rho_{o,T}$ and $\rho_{w,T}$ for $D_{o,T \text{ and } Dw,T}$. These calculations can also be performed by computer 84 or controller 86.

It is necessary to periodically update the variables $\rho_{o,T}$ and $\rho_{w,T}$ because these values change over the life of the producing well. Therefore, the FIG. 2 process includes a density determination mode beginning at Step P201. In step P201 controller 86 actuates one of the valves in manifold 22 (e.g., valve 32). The actuation diverts flow of materials from a selected well through the valve to test separator 24. The valve need not be actuated if the well is already flowing on test to separator 24, but it will normally be advantageous to enter the density determination mode prior to conducting an actual well test.

In Step P202; controller 86 opens dump valve 72 to permit flow of materials from valve 32 through test separator 24 and instrumentation drain line 26 into main production separator 42. Controller 86 uses liquid flowmeter 68 to measure a volume of total liquid sufficient to fill gathering line 38, test separator 24, and the portion of instrumentation drain line 26 preceding flowmeter 68. This volume flows through test separator 24, but does not fill test separator 24 because dump valve 72 remains open. A multiple of this volume may optionally be used to assure that test separator 24 has been fully purged of liquids from another well that did not flow through valve 32. This volumetric test separator purge operation provides significant advantages over conventional separator purge cycles that rely on a time of flow to purge the separator. Purge cycles that rely on time can result in the separator not being fully purged, and test measurements are eventually conducted on fluids from the wrong well. A volumetric purge assures that test measurements are eventually conducted on materials from the correct well.

In Step P204, controller 86 closes dump valve 72 to fill test separator 24 with liquid. At the same time, valve 32 is permitted to continue flowing material into test separator 24 until level indicator 46 provides a signal indicating to controller 86 that liquid within test separator 24 has reached a fill level. The fill level is preferably determined by the lease operator, and controller 86 or computer 84 can be programmed to fill test separator 24 to a different level for each producing well. The optimum fill level for each well is determined by experience in the field. The fill level is preferably based upon a total liquid level, but can also be based upon the oil or water level if a weighted float is used in level indicator 46. Gas flowmeter 60 measures the volumetric gas flow leaving test separator 24 during the fill process while gas flow control throttle valve 62 is adjusted by controller 86, as needed to maintain the materials within test separator 24 at a substantially constant pressure. Gas flowmeter 60 provides signals to controller 86 that indicate a volume of gas flowing through gas drain line 56.

When controller 86 receives the signal from indicator 46 that test separator 24 is sufficiently full, controller 86 causes valve 32 to divert its production to main production separator 42. Controller 86 also closes gas blanket valve 80 and gas flow control throttle valve 62 to seal the materials within test separator 24. The materials inside test separator 24 are permitted to settle while gravity segregates the respective oil, gas, and water components of the material inside test separator 24. The wait period for gravity segregation can be based upon a sufficient time, e.g., thirty minutes, as dictated by experience in the field. In the initial installation of system 20, the operator can view the separation within test separator 24 through a view window on level indicator 46. The required time for separation is provided as: program control data to computer. 84. The material within test separator 24 is permitted sufficient time for gravity to cause stratification of the different materials. This stratification normally does not need to occur within two please separator because the separator is only designed to measure two phase (gas and total liquid) flow.

The fill level within test separator 24 during gravity segregation preferably ranges from about 60% to about 80% of the internal volume of the separator. The drain level preferably drops down to about half of the separator internal volume. The respective fill and drain levels for test separator 24 are preferably different for each well, and can be programmed into computer 84. For example, a well that produces at a high water-cut and low production rate with little associated gas preferably is associated with a high fill level and a low drain level to optimized the produced oil volume in the separator. In comparison, a well that produces at a high gas-oil ratio and a high volumetric oil rate would preferably have a low fill level, and drain a very small volume down to the drain level to permit separation of the gas phase while not needing a significant drain volume to purge a segregated water phase beneath the oil.

In Step P206, after controller 86 has determined that the materials inside test separator 24 are sufficiently segregated, controller 86 opens dump valve 72 to drain the materials within test separator 24 through instrumentation drain line 26 and into main production separator 42. Valves 32 and 62 remain closed. The volume of materials that are drained from within test separator 24 is preferably kept relatively small, i.e., less than about five percent of the total separator volume (five barrels from a one-hundred barrel separator). In later steps, this small drainage volume permits rapid refilling of test separator 24 as needed to obtain an accurate well test of the daily rate for the well.

Step P208 includes obtaining measurements of the materials draining through line 26. Controller 66 receives signals from water-cut monitor 66 that indicate the water-cut of the liquids flowing through drain line 26. Similarly, controller 86 receives mass flow rate and density signals from liquid flowmeter 68. These signals can be converted into a volumetric flow rate either at flowmeter 68 or computer. 84. Controller 86 receives temperature signals from temperature monitor 69. Controller 86 closes dump valve 72 when controller 86 receives a signal from liquid level indicator 46 indicating that the liquid components have drained from within test separator 24 to a minimum level that avoids introducing gas into instrumentation drain line 26. Flowmeter 68 measures the density of the segregated materials that flow from test separator 24. The water density ($\rho_{w,T}$) is measured from water layer. 48, and will have the greatest density of any Component. This measurement is conducted on essentially pure water because the water component is substantially free of oil. The oil-in-water emulsion 50 normally causes extensive variations in the density measurement, and these values are ignored. The oil-in-water emulsion flow period is also characterized by a density less than water but greater than oil. Density measurements of the oil-in-water emulsion 50 are ignored. The oil layer 52 will have the lowest density value. The density measurement ($\rho_t$) of oil layer 52 must be corrected for residual water content because it typically contains up to about ten percent water.

The measured oil density is corrected for water content according to Equation (9) below:

$$\rho_{o,T} = (\rho_t - \rho_{w,T} WC)/(1-WC), \qquad (9)$$

wherein $\rho_{o,T}$ is water-corrected oil density at temperature T; $\rho$ the total density of the water-cut oil component as measured by the flowmeter 68 at temperature T; $\rho_w$ is the density of the water component as measured by the flowmeter 68 from the segregated water phase at temperature T; and WC is the water-cut of the oil component expressed as the volumetric fraction of water in the gravity-segregated oil component exiting test separator 24. WC is measured by the water-cut monitor 66. It is noted that the water-cut monitor 66 can be relied upon to obtain accurate water-cut readings because the water-cut in the segregated oil phase will typically not exceed 10%. The value $\rho_{o,T}$ is used in Equation (8), and the $X_w$ value from Equation (8) is used in combination with Equations (2)–(7) to provide volumetric rate calculations.

It is desirable to maintain a constant pressure inside test separator 24 during step P208 because excessively high or low pressures can result in volumetric test and density measurement errors as gas is liberated or absorbed by the separator liquids responsive to abnormal changes in pressure. Controller 86 monitors signals from pressure transmitter 58, and uses these signals to maintain a substantially constant pressure inside test separator 24. Controller 86 adjusts valve 80 to supply additional gas as needed to compensate for the pressure reduction that accompanies an expanding gas volume which compensates for the removal of liquids from within test separator 24. The pressure inside test separator 24 is preferably maintained at a value equal to or slightly above that for the main production separator 42. A slight additional pressure (e.g., +10 psi) will facilitate the flow of liquids through drain line 26 and into main production separator 42 without introducing a significant volumetric error. The pressure inside test separator 24 typically ranges from 200 psi to 1500 psi, plus or minus about 20 psi, but the pressure can be any pressure that circumstances demand.

In step P210, controller 86 determines whether the quantity of oil measured by liquid flowmeter 68 was a sufficient quantity from which to obtain an accurate reading. It is preferred to close valve 32 for very brief periods of time, so as to not interrupt the steady-state flow characteristics of the producing well with significant periods of pressure drawdown and buildup. Therefore, the draining of test separator 24 that occurs in step P208 is preferably limited to relatively small volumes of one to three barrels of total production. Controller 86 preferably requires a threshold volume to be produced, e.g., 100 barrels, before the test is completed. Volumetric measurements are taken over the time that the well is actually flowing. If the cumulative quantity of well test fluid is not sufficient, control transfers to step P212, which repeats the fill and drain cycles until a sufficient quantity of oil can be obtained for measurement. In this case, the signals from liquid level indicator 46 are received to indicate dumping of water to a minimum level that does not dump oil from within test separator 24 until steps P202 and P208 have been repeated a sufficient number of times to obtain a measurable quantity of oil. This feature of the processing avoids the need for the operator to purchase an oversize test separator merely for the purpose of obtaining a sufficient quantity of oil for measurement. Step P210 transfers control to step P214 once a sufficient quantity of oil has been obtained for measurement.

Step P214 concludes the density determination mode by returning control to Step P201. The cycle is preferably repeated until density measurements have been obtained from all of the flowing wells connected to manifold 22. Alternatively, Step P214 can return control to Step P200 for conducting a well test.

The test information derived from the above-described process includes water-cut data, volumetric gas flow rates, volumetric oil flow rate, volumetric water flow rate, oil density, water density, separator temperature, and separator pressure. Computer 84 stores these values for transmission to the operator. Alternatively, the data can be transmitted to the operator through a radio that is coupled with controller 86. The system advantageously permits more frequent and accurate well testing than can be obtained manually by pumpers who visit the production facility. The use of a Coriolis flowmeter (including a mass flowmeter and densitometer) as flowmeter 68 is particularly preferred because of its inherent accuracy and reliability.

It will be understood that numerous commercial sources exist for respective materials listed above. For example, several potential sources exist for electronically actuated three way valves such as valve 32, water-cut monitors such as monitor 66, and fluid level indicators such as indicator 46. The fact that Applicants have identified specific preferred commercial sources does not limit the practice of the invention to items obtained from these sources alone, because those skilled in the art are readily able to find and substitute substantially equivalent materials from alternative sources. Additionally, test separator 24 can be a conventional three-phase separator having a plurality of internal floats and drain ports for draining the respective phases. In this case, a separate liquid flowmeter 68 will be required for each drain line. In this application, the term 'oil' includes condensate from gas wells. It is not necessary that the well produce oil, water, and gas, but only that the mixture of wellhead production materials include a plurality of these different phases.

Those skilled in the art will understand that the preferred embodiments described hereinabove may be subjected to apparent modifications without departing from the scope and spirit of the invention. Accordingly, the inventors hereby state their full intention to rely upon the Doctrine of Equivalents in order to protect their full rights in the invention.

I claim:

1. An automatic well test system for determining the volume of respective components that are separated from a component mixture forming a wellhead production material, comprising:

means responsive to receipt of a wellhead production component mixture for separating said mixture into respective components thereof;

means for filling said separating means with said production component mixture to a fill level that permits said separating means to separate said wellhead production component mixture into respective components thereof, and for draining liquid components of said production component mixture from said separating means to a drain level, said liquid components including an oil component and a water component;

means for measuring a fluid density value and a mass flow rate value of each of said oil component and said water component as said draining means drains said liquid components from said separating means to arrive at said drain level;

means for correcting said measured fluid density value of said oil component by adjusting the same for water-cut within said oil component to provide a corrected oil component fluid density value, wherein said correcting means uses said fluid density value of said water component to correct said measured fluid density value of said oil component; and means for calculating a volumetric flow rate with respect to said oil component using said corrected oil component fluid density value.

2. The system as set forth in claim 1 wherein said measuring means includes a mass flowmeter and a densitometer for providing said mass flow rate values and said fluid density values.

3. The system as set forth in claim 1 wherein said draining means includes an electronically actuatable dump valve connected to said separator and said controlling means.

4. The system as set forth in claim 3 wherein said filling means includes a fluid level indicator connected to said separator and said controlling means for indicating said fluid level within said separator to said controlling means.

5. The system as set forth in claim 1 wherein said filling means includes an electronically actuatable valve coupled with a source of wellhead production fluids and said separating means.

6. The system as set forth in claim 1, wherein said measuring means includes a Coriolis mass flowmeter, a densitometer, and a water-cut monitor.

7. The system as set forth in claim 1 wherein said filling means and said draining means include means for repeatably filling said wellhead separating means by adding said wellhead production component mixture to reach said predetermined fill level and draining said liquid components from said separating means.

8. A method of operating an automatic well test system to measure the volume and density of respective components that are separated from a component mixture forming a wellhead production material, said method comprising the steps of:

supplying a wellhead production component mixture for use in a separator;

filling said separator with said production component mixture to a fill level for separation of said wellhead production component mixture by said separator, said production component mixture including a water component and an oil component;

draining liquid components of said production component mixture from said separator to a drain level;

measuring a fluid density value, a mass flow rate, and a water-cut value respectively of said liquid components after said draining means drains said liquid components from said separating means to arrive at said drain level;

correcting said fluid density value measured on said oil component by adjusting the same for water-cut within said oil component to provide a corrected oil component fluid density value, where said fluid density value of said water component is used to correct said measured fluid density value of said oil component; and using said corrected oil component fluid density value and said mass flow rate to calculate a volumetric flow rate with respect to said oil component.

9. A method of operating an automatic Well test system to measure the volume and density of respective components that are separated from a component mixture forming a wellhead production material, said method comprising the steps of:

supplying a wellhead production component mixture for use in a separator;

filling said separator with said production component mixture to a fill level for separation of said wellhead production component mixture by said separator, said production component mixture including a water component and an oil component;

draining liquid components of said production component mixture from said separator to a drain level;

measuring a fluid density value, a mass flow rate, and a water-cut value respectively of said liquid components after said draining means drains said liquid components from said separating means to arrive at said drain level;

correcting said fluid density value measured on said oil component by adjusting the same for water-cut within said oil component to provide a corrected oil component fluid density value; and using said corrected oil component fluid density value and said mass flow rate to calculate a volumetric flow rate with respect to said oil component, said correcting step including correction according to a formula $$\rho_{o,T} = (\rho_t - \rho_{w,T} WC)/(1 - WC),$$

wherein $\rho_o$ is said corrected oil component fluid density value at a temperature T; $\rho_t$ is a total density of the segregated oil component including residual water as measured by said densitometer at temperature T; $\rho_{w,T}$ is the density of the water component as measured by said densitometer on a segregated water phase; and WC is the water-cut of the segregated oil component including residual water expressed as a volumetric fraction of water in the segregated oil component.

10. A method of operating an automatic well test system to measure the volume and density of respective components that are separated from a component mixture forming a wellhead production material, said method comprising the steps of:

supplying a wellhead production component mixture for use in a separator;

filling said separator with said production component mixture to a fill level for separation of said wellhead production component mixture by said separator, said production component mixture including a water component and an oil component;

draining liquid components of said production component mixture from said separator to a drain level;

measuring a fluid density value, a mass flow rate, and a water-cut value respectively of said liquid components after said draining means drains said liquid components from said separating means to arrive at said drain level;

correcting said fluid density value measured on said oil component by adjusting the same for water-cut within said oil component to provide a corrected oil component fluid density value, where said fluid density value of said water component is used to correct said measured fluid density value of said oil component; and using said corrected oil component fluid density value and said mass flow rate to calculate a volumetric flow rate with respect to said oil component, wherein said draining step includes providing a pressurized gas blanket over the materials within said separator to prevent flashing said materials when said liquid components are being drained from said separator.

11. The method as set forth in claim 10 including a step of refilling said separating means with said wellhead production component mixture to said fill level after said draining means has drained said separating means to said drain level, and repeating said draining step until a sufficient quantity of said oil component has been obtained to permit said measuring step to occur.

12. An automatic well test system for determining the volume of respective components that are separated from a component mixture forming a wellhead production material, comprising:

means responsive to receipt of a wellhead production component mixture for separating said mixture into respective components thereof;

means for filling said separating means with said production component mixture to a fill level that permits said separating means to separate said wellhead production component mixture into respective components thereof, and for draining liquid components of said production component mixture from said separating means to a drain level, said liquid components including an oil component and a water component;

means for measuring a fluid density value and a mass flow rate value of each of said oil component and said water component as said draining means drains said liquid components from said separating means to arrive at said drain level;

means for correcting said measured fluid density value of said oil component by adjusting the same for water-cut within said oil component to provide a corrected oil component fluid density value; and means for calculating a volumetric flow rate with respect to said oil component using said corrected oil component fluid density value, said measuring means including a mass flowmeter and a densitometer for providing said mass flow rate values and said fluid density values, said correcting means including a control program providing means for calculating according to a formula $$\rho_{o,T} = (\rho_t - \rho_{w,T} WC)/(1-WC),$$

wherein $\rho_o$ is said corrected oil component fluid density value at a temperature T; $\rho_t$ is a total density of the segregated oil component including residual water as measured by said densitometer at temperature T; $\rho_{w,T}$ is the density of the water component as measured by said densitometer on a segregated water phase; and WC is the water-cut of the segregated oil component including residual water expressed as a volumetric fraction of water in the segregated oil component.

13. The system as set forth in claim 12 wherein said measuring means includes a water-cut monitor for providing said water-cut values, said water-cut monitor being effective for providing accurate water-cut values within a range up to about thirty percent water.

14. An automatic well test system for determining the volume of respective components that are separated from a component mixture forming a wellhead production material, comprising:

means responsive to receipt of a wellhead production component mixture for separating said mixture into respective components thereof;

means for filling said separating means with said production component mixture to a fill level that permits said separating means to separate said wellhead production component mixture into respective components thereof, and for draining liquid components of said production component mixture from said separating means to a drain level, said liquid components including an oil component and a water component;

means for measuring a fluid density value and a mass flow rate value of each of said oil component and said water component as said draining means drains said liquid components from said separating means to arrive at said drain level;

means for correcting said measured fluid density value of said oil component by adjusting the same for water-cut within said oil component to provide a corrected oil component fluid density value, where said fluid density value of said water component is used to correct said measured fluid density value of said oil component; and means for calculating a volumetric flow rate with respect to said oil component using said corrected oil component fluid density value; and wherein said separating means includes means for preventing flash-removal of a gas component from said wellhead production fluid when said draining means is draining liquid components from said separator.

15. The system as set forth in claim 14 wherein said preventing means includes a gas blanket valve connecting a pressurized gas source with said separator, said gas blanket valve providing means for supplying gas from said pressurized gas source to said separator at a pressure that prevents flashing of liquid within said separator.

* * * * *